US00PP15787P3

(12) United States Plant Patent
Yatabe

(10) Patent No.: US PP15,787 P3
(45) Date of Patent: Jun. 7, 2005

(54) ***HYDRANGEA MACROPHYLLA* PLANT NAMED 'RIPPLE'**

(50) Latin Name: *Hydrangea macrophylla*
Varietal Denomination: Ripple

(76) Inventor: Mototeru Yatabe, 20 Shioyama, Kanuma City, Tochigi Prefecture (JP), 522-0627

( * ) Notice: Subject to any disclaimer, the term of this patent is extended or adjusted under 35 U.S.C. 154(b) by 0 days.

(21) Appl. No.: 10/445,433

(22) Filed: May 27, 2003

(65) Prior Publication Data

US 2004/0244081 P1 Dec. 2, 2004

(51) Int. Cl.[7] ..... A01H 5/00
(52) U.S. Cl. ..... Plt./250
(58) Field of Search ..... Plt./250

*Primary Examiner*—Kent Bell
(74) *Attorney, Agent, or Firm*—Jondle & Associates P.C.

(57) ABSTRACT

Ripple is a new variety of *Hydrangea* plant. This new variety has white flowers with red margins.

2 Drawing Sheets

Genus/species: *Hydrangea macrophylla.*

BACKGROUND OF THE INVENTION

The present invention relates to a new and distinct variety of *Hydrangea macrophylla* plant named 'Ripple'.

The genus *Hydrangea* is included in the family Saxifragaceae which comprises about 80 genera and 1,200 species of herbs, shrubs, small trees, and woody climbers mostly temperate in origin. *Hydrangea* comprises approximately 23 species of deciduous or evergreen shrubs and vines originating in North America, South America and East Asia, many of which possess desirable ornamental characteristics. Recent taxonomical treatments sometimes isolate *Hydrangea* in a new family, Hydrangeaceae.

*Hydrangea macrophylla* is widespread and common throughout much of Japan. It generally has opposite, simple leaves, obovate to elliptic in shape, 10 to 20 cm long and 5 to 15 cm wide. Leaf color ranges from light to dark green, depending on light intensity and cultural conditions. Leaves are generally softly pubescent. Flower color is dependent upon the pH level of the soil and the amount of available aluminum in the soil media. Flowers of *Hydrangea macrophylla* are borne in mostly sterile florets, formed in what is often called a "hortensia" flower.

SUMMARY OF THE INVENTION

The new variety exhibits white to chartreuse florets with red margins throughout the growing season. The new plant was bred in Kanuma-City, Japan. The female parent is *Hydrangea macrophylla* 'Love You Kiss' and the male parent is *Hydrangea macrophylla* "Mirai." Asexual reproduction of the new variety by stem cuttings in both Kanuma-City, Japan and in Huissen, The Netherlands has confirmed that the distinctive characteristics of the new variety are stable and transmitted to succeeding generations and the new variety reproduces true to type.

BRIEF DESCRIPTION OF THE ILLUSTRATIONS

The accompanying illustrations show specimens of the new cultivar in photographic illustrations as true to color as is reasonably possible to make in photographs of this character.

DETAILED DESCRIPTION OF THE NEW PLANT

Figure 1:
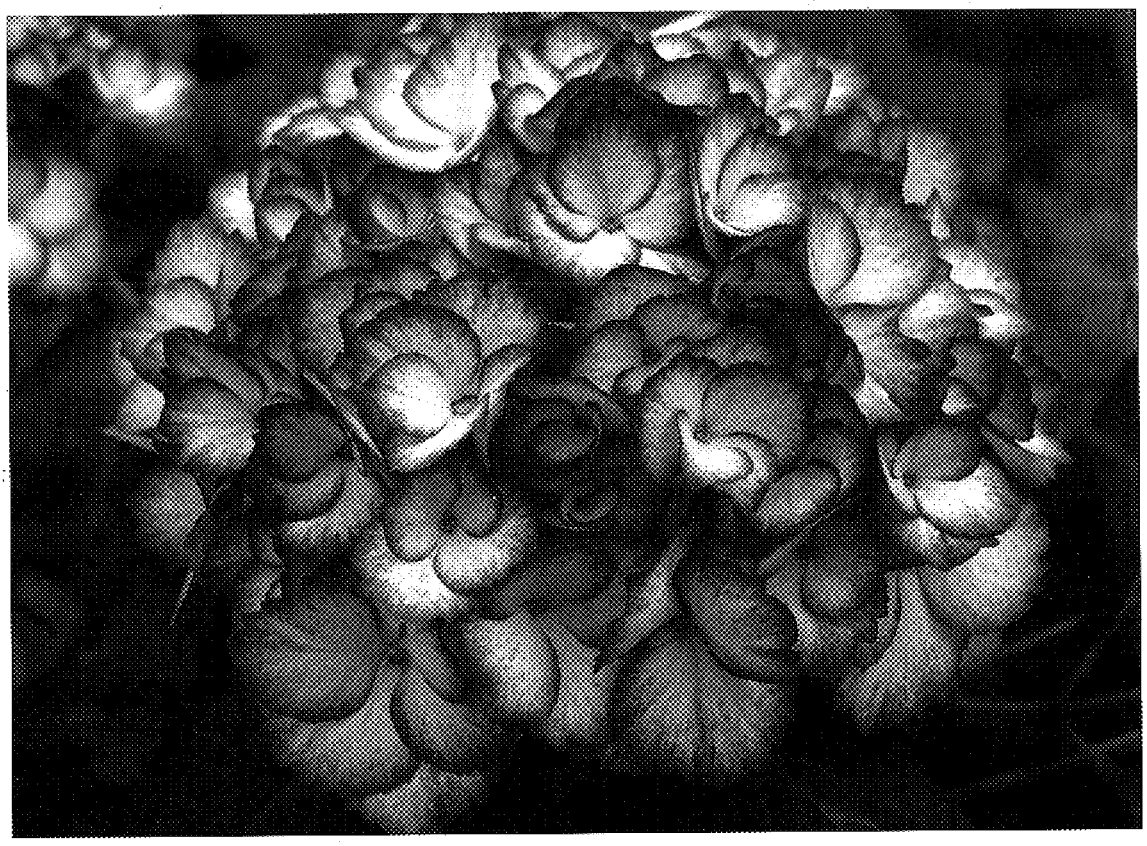
FIG. 1 is a close-up view of the inflorescence.
Figure 2:
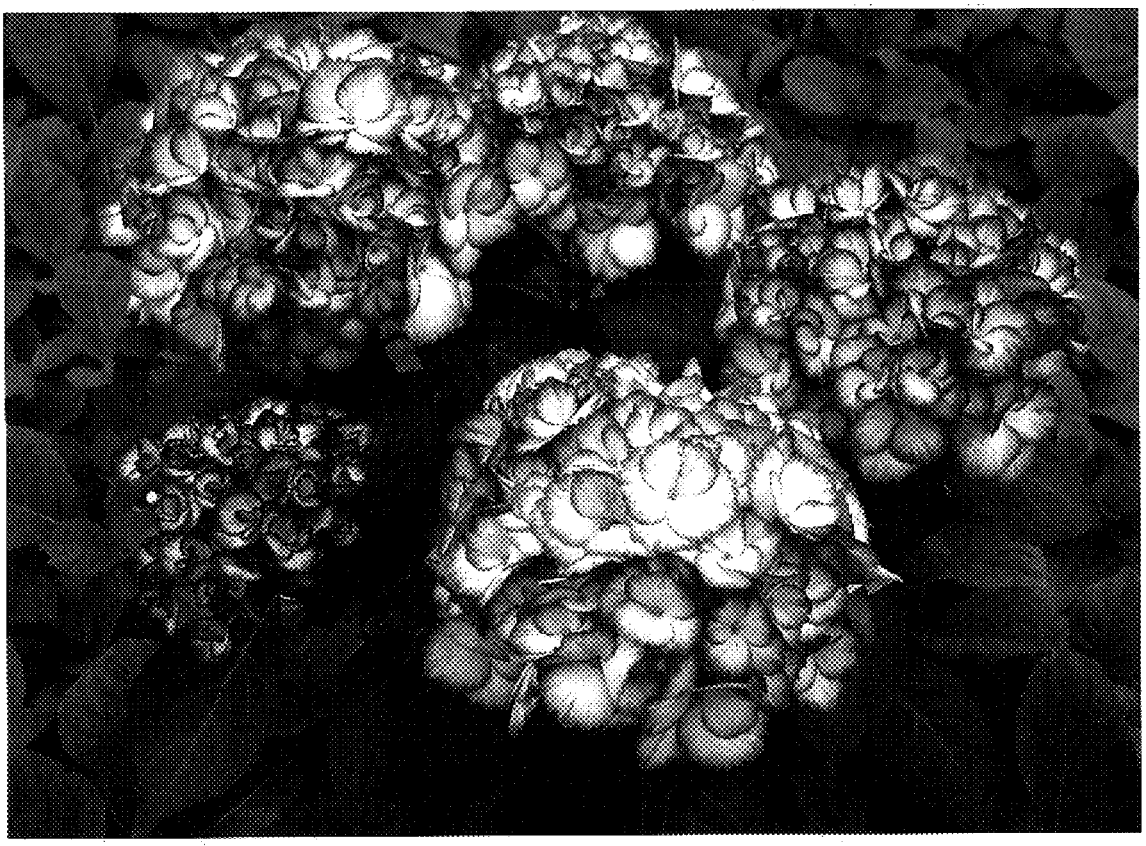
FIG. 2 is a view of a typical flowering plant of 'Ripple'.

The following observations and descriptions are of 14–16 month old plants grown in 14 cm containers in Kanuma-City, Japan and of 15 month old plants grown in 14 cm containers in Huissen, The Netherlands. The plants were grown in greenhouses in both Japan and The Netherlands. In this description, color references are to The Royal Horticultural Society Colour Chart (2001) and The Japanese Horticultural Society Color Chart and terminology used in the color descriptions herein refers to plate numbers in this color chart.

Classification:

*Family.*—*Hydrangea.*
*Species.*—*Macrophylla.*
*Common name.*—*Hydrangea.*
*Parentage.*—Male parent — *Hydrangea macrophylla* 'Mirai' Female parent — *Hydrangea macrophylla* 'Love You Kiss'.

Plant:

*Propagation.*—Plants of this variety are grown from cuttings taken from motherplants in February, March or early April. Growth retarders are used during the culture.

*Height.*—At the end of the first growing season, about October of that same year, the plants have a height of 10–15 cm above the soil/container and 5–8 branches. The diameter of the plants is about 15–20 cm when the leaves are still on the plant.

*Time to flowering.*—These plants can be forced into flower in heated greenhouses and need until March before they flower. When grown in unheated greenhouses they will need until May or early June to flower. At that time the height above the soil/container is approximately 30–35 cm and the diameter is 40–50 cm. Also at that time the plant has 4–7 flower heads and branches have a diameter of 6–7 mm.

*Branch length.*—When the plant is about 35 cm tall, the branch length is 15–20 cm.

Branching:
*Habit.*—Medium.
*Fasciation.*—None.
*Twisting.*—None.
*Thickness.*—Medium.
*Internode length.*—Observed 4–8 cm.
*Flowering branch color.*—RHS 137A to 138A.
*Spot.*—1–2 mm long; 40–65 spots per internode; 4–5 internodes per branch; 160–325 spots per branch.
*Color of branch spot.*—RHS 59A and 187B.
*Color.*—Branch color of previous year; darker parts are RHS 166A and 200B; lighter parts are RHS 177C and 174A.
*Phyllotaxis.*—Opposite.

Leaves:
*Shape.*—Elliptical.
*Apex.*—Acute.
*Base.*—Obtuse.
*Margin.*—Serrate.
*Size.*—Medium.
*Length.*—13–16 cm.
*Width.*—6–7 cm.
*Thickness.*—Medium.
*Premature leaf color.*—Upper surface — RHS 137A. Lower surface — RHS 147B and 148A. On the border of the leaves (lower surface) there is a shine of color RHS 61A over it.
*Mature leaf color.*—Upper surface — RHS 135A and 139A. Lower surface — RHS 137C, 138A and 147B.
*Variegation.*—None.
*Autumn tints of leaf.*—Absent.
*Gloss of leaf color.*—None.
*Gloss of leaf underside.*—None.
*Hair on leaf surface.*—None.
*Hair on leaf underside.*—None.
*Petiole thickness.*—0.6 cm.
*Petiole length.*—1.6 cm.
*Petiole color.*—Upper surface RHS 146B, lower surface RHS 138B and 139C.
*Petiole hair.*—None.

Inflorescence:
*Type.*—Compound corymb.
*Shape.*—Spheroidal.

Flowers:
*Form.*—Hortensias.
*Direction.*—Upward.
*Node number of stem to flowering.*—5.
*Longitudinal length of inflorescence.*—19 cm.
*Horizonal length of inflorescence.*—18 cm.
*Thickness of inflorescence.*—9 cm.
*Height of inflorescence.*—10 cm.
*Number of fertile flowers.*—10–20 per inflorescence.
*Number of sterile flowers.*—110–120 per inflorescence.
*Diameter of fertile flower.*—0.4 cm.
*Color of fertile flower.*—RHS 58A, RHS 57A, RHS 57B and RHS 46B.
*Fertile flower.*—Single.
*Sterile flower.*—Normal Flat.
*Number of inflorescences per plant.*—12–18 per plant per year.
*Flower longevity.*—12–14 weeks calculated from 6 weeks for the white/red phase and 6–8 weeks for the green phase.

Sepal:
*Sepal.*—Overlap.
*Size difference in sepal.*—A little.
*Length of sterile flowers.*—5.5–6.0 cm.
*Sterile flower color.*—Multicolor.
*Multicolored pattern of sterile flowers.*—Margin colored.
*Color of sterile flowers at the beginning of flowering.*—JHS 3305 (green).
*Color of sterile flowers in full bloom.*—JHS 3101 (white).
*Sepal color.*—Center of sepal of flower in full bloom on both upper and lower surfaces is RHS 155D; rim of upper surface is RHS 60C, 61B and 63A; rim of lower surface is RHS 63A, 63B, 61C, 60D and 59D.
*Secondary color of sterile flowers.*—JHS 9506 (crimson).
*Sepal shape.*—Base: Attenuate; apex: obtuse; margins are between serrate and crenate.
*Position of sepal incision.*—Middle part.
*Density of sepal incision.*—Low.
*Type of sepal incision.*—Obtuse.
*Number of sepals.*—4–5.
*Sepal length.*—3 cm.
*Sepal width.*—3 cm.

Peduncle:
*Peduncle length.*—6 cm.
*Peduncle diameter.*—3–4.5 mm.
*Peduncle color.*—JHS 3305 (light green).
*Peduncle number.*—5.

Pedicel:
*Pedicel length.*—3 cm.
*Pedicel diameter.*—1.5 mm.
*Pedicel color.*—JHS 2901 (yellowish-white).

Reproductive organs:
*Stamen number.*—8–12.
*Pistil number.*—3–5 pistils per flower.
*Filament color.*—RHS 155D under greenhouse conditions.
*Anther color.*—RHS 155D under greenhouse conditions.
*Fruit shape.*—Round.
*Fruit color.*—Brown.
*Fragrance.*—Absent.

Disease/pest resistance: Plants of the new variety have been observed to be significantly more susceptible to *Botrytis* than the average *Hydrangea macrophylla.* No susceptibility or resistance to other diseases or pests beyond that of the species has been noted.

What is claimed is:

1. A new and distinct *Hydrangea* plant as shown and described herein.

* * * * *